(12) United States Patent
Veen et al.

(10) Patent No.: US 8,447,372 B2
(45) Date of Patent: May 21, 2013

(54) MONITORING A VITAL PARAMETER OF A PATIENT WITH "IN-SITU" MODULATION SCHEME TO AVOID INTERFERENCE

(75) Inventors: Jeroen Veen, Eindhoven (NL); Theodorus Petrus Henricus Gerardus Jansen, Eindhoven (NL); Henricus Renatus Martinus Verberne, Eindhoven (NL); Tim Corneel Wilhelmus Schenk, Eindhoven (NL); Lorenzo Feri, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 204 days.

(21) Appl. No.: 12/996,991

(22) PCT Filed: Jun. 9, 2009

(86) PCT No.: PCT/IB2009/052435
§ 371 (c)(1), (2), (4) Date: Dec. 9, 2010

(87) PCT Pub. No.: WO2009/153700
PCT Pub. Date: Dec. 23, 2009

(65) Prior Publication Data
US 2011/0092824 A1    Apr. 21, 2011

(30) Foreign Application Priority Data
Jun. 16, 2008 (EP) .................... 08104427

(51) Int. Cl.
*A61B 5/00* (2006.01)
(52) U.S. Cl.
USPC ................ 600/310; 600/340; 250/201.1
(58) Field of Classification Search
USPC ............. 600/310, 340, 476; 250/201.1, 205, 250/226
See application file for complete search history.

(56) References Cited

U.S. PATENT DOCUMENTS

| | | | |
|---|---|---|---|
| 5,995,858 A | 11/1999 | Kinast | |
| 6,505,133 B1 * | 1/2003 | Hanna et al. | 702/74 |
| 7,003,339 B2 * | 2/2006 | Diab et al. | 600/336 |
| 7,194,292 B2 * | 3/2007 | Norris | 600/323 |
| 7,328,053 B1 | 2/2008 | Diab et al. | |
| 7,729,732 B2 * | 6/2010 | Ohashi | 600/310 |
| 2003/0028357 A1 | 2/2003 | Norris et al. | |
| 2006/0111623 A1 | 5/2006 | Stetson et al. | |
| 2006/0222224 A1 * | 10/2006 | Ohashi | 382/128 |

FOREIGN PATENT DOCUMENTS
DE      102006022120 A1    9/2007

* cited by examiner

*Primary Examiner* — Unsu Jung
*Assistant Examiner* — Saurel J Selkin

(57) ABSTRACT

The invention relates to a method of monitoring a vital parameter of a patient by measuring attenuation of light emitted onto tissue of the patient, comprising the following steps: modulating the light with a modulation frequency or/and a modulation code; emitting the modulated light onto the tissue of the patient; collecting light which is transmitted through the tissue or/and which is reflected from the tissue; demodulating the collected light; analyzing the demodulated collected light with regard to interference with ambient light; determining a modulation frequency or/and a modulation code for which interference with the ambient light is minimized or falls under a predefined threshold; and setting the modulation frequency or/and the modulation code for modulating the light according to the determined modulation frequency or/and a modulation code for which interference with the ambient light is minimized or falls under a predefined threshold. In this way a versatile and reliable possibility of monitoring a vital parameter of a patient with a high signal-to-interference ratio is provided.

20 Claims, 3 Drawing Sheets

MONITORING A VITAL PARAMETER OF A PATIENT WITH "IN-SITU" MODULATION SCHEME TO AVOID INTERFERENCE

FIELD OF THE INVENTION

The invention relates to the field of light attenuation measurements, and especially to a method of and a device for monitoring a vital parameter of a patient by measuring attenuation of light emitted onto tissue of the patient

BACKGROUND OF THE INVENTION

The measurement of light absorption and/or scattering when propagating through or reflecting from a certain medium forms the basis of a number of optical spectroscopic methods widely applied in various medical domains, such as patient monitoring. An illustrative example is transmissive pulse oximetry.

Pulse oximetry is an optical method for non-invasive monitoring of arterial oxygen saturation of a patient and has become one of the most commonly used technologies in clinical practice. The protein haemoglobin (Hb) binds oxygen in the red blood cells for transport through the body, and has the property of changing from dark red to bright red in colour when oxygenated. By emitting and detecting light at two or more wavelengths, pulse oximeters determine the light absorbance in a peripheral vascular bed to arrive at an indirect estimate of oxygen saturation, i.e. the concentration fraction of oxyhaemoglobin ($HbO_2$). Pulse oximeters rely on the changes in arterial blood volume caused by cardiac contraction and relaxation to determine the amount of light absorbed by pulsating arterial blood alone, thereby largely factoring out the contributions of tissue and venous blood.

In many applications, including oximetry, simultaneous or quasi-simultaneous attenuation measurements of an optical path at different wavelengths, i.e. of different colours, are required. To that end, typically multiple light sources are utilized which are generally combined with a single photo-detector. In order to be able to distinguish between the signals from each of the emitters at the photo-detector, in general, electrical multiplexing methods are employed, such as time division multiplexing (TDM), frequency division multiplexing (FDM), or code division multiplexing (CDM).

In the medical practice, light attenuation measurements applied in e.g. patient monitoring suffer from electromagnetic interference. Typically such interference consists of ambient light at various optical wavelengths and with different modulation frequencies. Common examples include natural daylight, which is typically not modulated, as well as artificial light from incandescent lamps, which is modulated at the double mains frequency (100 Hz or 120 Hz) and 50 Hz or 60 Hz harmonics, and from fluorescent lamps with flicker rates ranging from tens to hundreds of kilohertz depending on the specific electronic ballast.

Generally, in spectrometric devices measures are taken to mitigate the effect of external interference on the measurements. For example in pulse oximeters, the light sources are modulated such that at the photo-detector the emitted light can be distinguished from ambient light by filtering or demodulation. Regardless of the modulation techniques applied, conventional methods rely on knowledge of the spectral modulation of the environmental light and assume that the light source modulation frequency or band that is used can remain fixed for the lifetime of the device. However, if the ambient light modulation spectrum is only partly or not known a priori, such as is the case when the spectrometric device operates in the vicinity of light communication systems, then interference may be present in the modulation spectrum of the detected light at the device operation frequency. Similarly, new operation schemes of high-intensity discharge (HID) lamps might result in interference signal with a wide frequency range. Moreover, emerging light emitting diodes (LEDs) light sources are foreseen to use a wide range of modulation frequencies, creating new sources of interferences. If an interferer contaminates the operation frequency band, the signal-to-interference ratio (SIR) may decrease to a large extent, thereby degrading the measurement quality.

SUMMARY OF THE INVENTION

It is an object of the invention to provide such a method of monitoring a vital parameter of a patient by measuring attenuation of light emitted onto tissue of the patient and an according device which allow for a high signal-to-interference ratio in a versatile and reliable way.

This object is achieved by a method of monitoring a vital parameter of a patient by measuring attenuation of light emitted onto tissue of the patient, comprising the following steps:

modulating the light according to a modulation mode;
emitting the modulated light onto the tissue of the patient;
collecting ambient light and/or light which is transmitted through the tissue and/or light which is reflected from the tissue;
demodulating the collected light according to the modulation mode;
analyzing the demodulated collected light with regard to the contribution of the ambient light;
determining a modulation mode for which the contribution of the ambient light is minimized or falls under a predefined threshold; and
setting the modulation mode for modulating the light according to the determined modulation mode for which the contribution of the ambient light is minimized or falls under a predefined threshold.

According to the invention, light which is transmitted through the tissue or/and which is reflected from the tissue is collected which is necessary for the attenuation measurement in order to monitor the vital parameter of the patient. However, when collecting this light, it cannot totally be avoided to collect at least some ambient light, too. Thus, the step of "collecting ambient light" does not mean that special measures have to be taken in order to collect this ambient light. Though, of course, it lies within the scope of the invention to take such measures, ambient light will always be collected when transmitted and/or reflected light is collected. Further, if no transmitted and/or reflected light exists since no light is emitted, ambient light can be collected, too. This means that above mentioned steps of the method according to the invention do not have to be executed simultaneously. Especially, this means that the step of "collecting ambient light and/or light which is transmitted through the tissue and/or light which is reflected from the tissue" can be executed during the emission of modulated light and/or in a time period in which no modulated light is emitted and, thus, only ambient light is collected.

Hence, it is an important idea of the invention to adapt the modulation scheme during operation, i.e. "in-situ", to the modulation spectrum of the ambient light. Due to setting the modulation scheme, i.e. the modulation frequency or the modulation code, "in-situ" according to the interference with the ambient light which is determined "in-situ" on the basis of the contribution of the ambient light, the negative impact of the ambient light on the signal-to-interference ratio is greatly reduced.

It should be emphasized that the term "patient" does not only refer to diseased persons but to all human beings and animals, no matter whether healthy or not.

In general, there are different ways for performing the invention. However, according to a preferred embodiment of the invention, the modulation mode is a modulation frequency or/and a modulation code.

Further, according to a preferred embodiment of the invention, the step of emitting light onto the tissue of the patient is interrupted for a predefined interruption time period, during this interruption time period the collected light is successively demodulated with different modulation frequencies, and the modulation frequency for which the output of demodulating the collected light is minimized or falls under a predefined threshold is determined to be the modulation frequency for the light emitted onto the tissue of the patient after the predefined interruption time period. Thus, according to this preferred embodiment of the invention, the fact is used that the method can be operated at different frequencies, i.e. different FDM modes. Preferably, these different FDM modes are approximately, most preferably exactly, orthogonal to each other in the frequency domain.

With respect to this preferred embodiment of the invention it is further preferred that the different modulation frequencies are a discrete set of frequencies or are continuous within a predefined range. Further, the step of emitting light onto the tissue of the patient is preferably interrupted periodically. Furthermore, instead of alternatingly changing between attenuation measurements and frequency adaptation, it is preferred that an adaptation phase is initiated based on the analysis of the demodulator output.

According to another preferred embodiment of the invention, the step of emitting light onto the tissue of the patient is interrupted for a predefined interruption time period, during this interruption time period the collected light is successively demodulated with different modulation codes, and the modulation code for which the output of demodulating the collected light is minimized or falls under a predefined threshold is determined to be the modulation code for the light emitted onto the tissue of the patient after the predefined interruption time period.

Further, similar to the preferred embodiment of the invention described before, the step of emitting light onto the tissue of the patient is preferably interrupted periodically. Furthermore, instead of alternatingly changing between attenuation measurements and code adaptation, it is preferred that an adaptation phase is initiated based on the analysis of the demodulator output.

Moreover, with respect to using modulation codes instead of modulation frequencies, in the case that the step of analyzing the demodulated collected light with regard to the contribution of the ambient light yields a lower level of contribution, a shorter modulation code is applied; and in the case that the step of analyzing the demodulated collected light with regard to contribution of the ambient light yields a higher level of contribution, a longer modulation code is applied.

Further, according to a preferred embodiment of the invention, the step of emitting light onto the tissue of the patient is interrupted for a predefined interruption time period, during this interruption time period the power spectrum of the collected light is determined using a Fourier transform, and the frequency for which the power spectrum is determined to have its minimum or a frequency for which the power spectrum falls below a predefined threshold is determined to be the modulation frequency for the light emitted onto the tissue of the patient after the predefined interruption time period. Thus, this preferred embodiment of the invention is related to directly evaluating the spectrum of the collected light, i.e. before demodulation. Also with respect to this preferred embodiment it is further preferred that the step of emitting light onto the tissue of the patient is periodically interrupted.

According to another preferred embodiment of the invention, the modulation frequency of the light emitted onto the tissue is consecutively changed by cycling through a predefined set of at least two frequency modes or frequency bands; and the modulation frequency for which the output of demodulating the collected light is maximized or exceeds a predefined threshold is determined to be the active modulation frequency for the light emitted onto the tissue of the patient. This preferred method is also referred to as frequency hopping.

In this case, the set of frequencies is preferably adapted in order to avoid interference by modulated ambient light. Generally, it can be expected that the ambient light modulation spectrum does not cover the entire frequency set, and it can be assumed that at least one of the modulation frequencies is free of interference. To that end, the frequency set is preferably chosen such that a high spectral diversity is guaranteed. Therefore the detected light for at least one of the frequencies in the set, i.e. the one that is free of disturbance, results in a maximum attenuation measurement. For a given colour of light, attenuation measurements are independent of the modulation frequencies. If another frequency in the set results in a lower attenuation measurement, this is a result of interference in that modulation frequency band, and the corresponding frequency is preferably replaced.

In principle, a new frequency in the set can be chosen arbitrarily or based on some selection criterion. Preferably, spectral sensing, as described before, is applied to select the initial set for frequency hopping and also to replace frequencies in the set. In case of this preferred embodiment of the invention, emitting the light onto the tissue of the patient is preferably not interrupted. Preferably, a new modulation frequency or set is selected while another modulation frequency is used. Further, it is especially preferred, that a set of only two frequencies is used, wherein the second modulation frequency is chosen from the spectrum when the attenuation is measured using the first frequency and vice versa, thereby continuously seeking the optimal modulation frequency.

The advantage of adaptive modulation frequency hopping is that the method is based on the quasi-simultaneous evaluation of the received signal at multiple frequencies, thereby allowing continuous measurement without interruption by an adaptation phase.

Above mentioned object is further addressed by a device for monitoring a vital parameter of a patient by measuring attenuation of light emitted onto tissue of the patient, with
- a light modulator adapted for modulating the light according to a modulation mode;
- a light emitter adapted for emitting the modulated light onto the tissue of the patient;
- a light detector adapted for light which is transmitted through the tissue or/and which is reflected from the tissue and unavoidably being adapted for collecting ambient light;
- a light demodulator adapted for demodulating the collected light according to the modulation mode;
- an interference analyzer adapted for analyzing the demodulated collected light with regard to the contribution of the ambient light; and a processing unit adapted for determining a modulation mode for which the contribution of the ambient light is minimized or falls under a predefined threshold and for setting the modulation mode for modulating the light according to the determined modulation mode for which the contribution of the ambient light is minimized or falls under a predefined threshold.

With respect to the device according to the preferred embodiment of the invention, this device is adapted for emitting light with at least two different wavelengths. Further, it is especially preferred that the device is a pulse oximeter.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

According to an embodiment of the invention, instead of fixing the light modulation frequency bands upon manufacturing of the attenuation measurement device, the modulation scheme is adapted "in-situ" to the modulation spectrum of the ambient light. This modulation scheme is realized by actively monitoring the ambient light or the effect thereof on the detection performance, and changing the transmission and/or detection parameters such that interference with modulated ambient light is avoided or suppressed.

Figure 1:
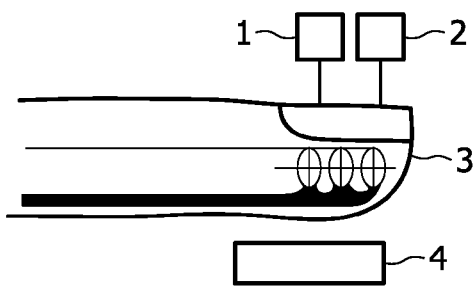
FIG. 1 shows a typical setup for transmission pulse oximetry.

FIG. 1 shows a typical setup for transmission pulse oximetry: A red light source 1 and an infrared (IR) light source 2 are used for irradiating red light of 660 nm and IR light of 940 nm onto tissue of a patient, i.e. onto a finger 3. The part of the light which is transmitted through the finger 3 is then collected with a common light detector 4.

Figure 2:
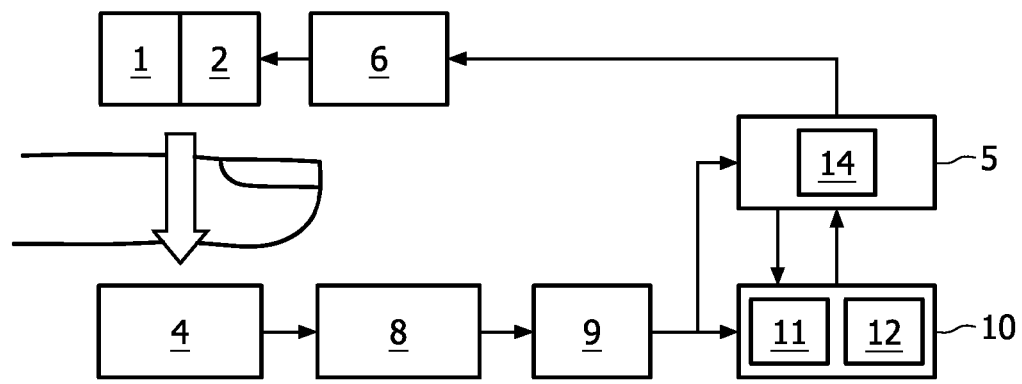
FIG. 2 depicts a generalized block diagram of a transmission pulse oximetry method according to an embodiment of the invention.

FIG. 2 depicts a general block diagram of a transmission pulse oximeter according to an embodiment of the invention. The system comprises a processing unit 5 that adjusts the parameters of a light modulator 6 which acts a pulse controller and modulates the light sources 1, 2. The configuration of the light modulator 6 depends on the specific multiplexing scheme applied, e.g. in case of TDM the light sources 1, 2 are activated alternatingly, whereas for FDM the light sources 1, 2 radiate light simultaneously but with different modulation frequencies. The reason for the multiplexing scheme is that in this way the same light detector 4 can be used to estimate the attenuation of the light from both light sources 1, 2.

The light detector 4 detects the light that has propagated through the medium of the finger 3 and converts it into an electrical signal. This signal is then pre-processed by a signal-conditioning block 8, which comprises analog amplifiers and band-pass filters, which make the signal suitable for conversion to the digital domain by an analog-to-digital converter (ADC) 9. Correlators 10, each comprising a demodulator 11 and a demultiplexer 12, are used to simultaneously demodulate and demultiplex the detected light, and the results are presented to the processing unit 5, which determines the parameters of interest by evaluating the transmitted and demodulated signals. For that, the processing unit comprises an interference analyzer 14.

Figure 3:
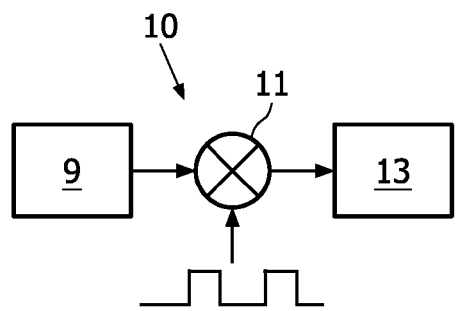
FIG. 3 shows a demodulator with a periodic square wave reference signal.

The scheme according to the embodiment of the invention is independent of the specific multiplexing technique applied, since all attenuation measurement methods incorporate a certain modulation method. To simplify matters, the description of the following embodiments is restricted to a single light source, thereby disregarding the specific demultiplexing method. For a single light source, only one correlator 10 is necessary. This correlator 10 then simply equals a demodulator 11, such as depicted in FIG. 3. Here, the information on the light attenuation becomes present in the base-band by multiplying the received signal with a local reference of the same fundamental frequency ($fm=1/Tm$). Subsequently, only the base-band signal is preserved by passing the signal through a low-pass filter 13, thereby disregarding out-of-band interference.

It should be noted that the square wave in FIG. 3 is only illustrative, as any periodic signal can be applied to both modulate the light sources 1, 2 and demodulate the received signal as long as the fundamental frequencies and/or harmonics coincide.

Figure 4:
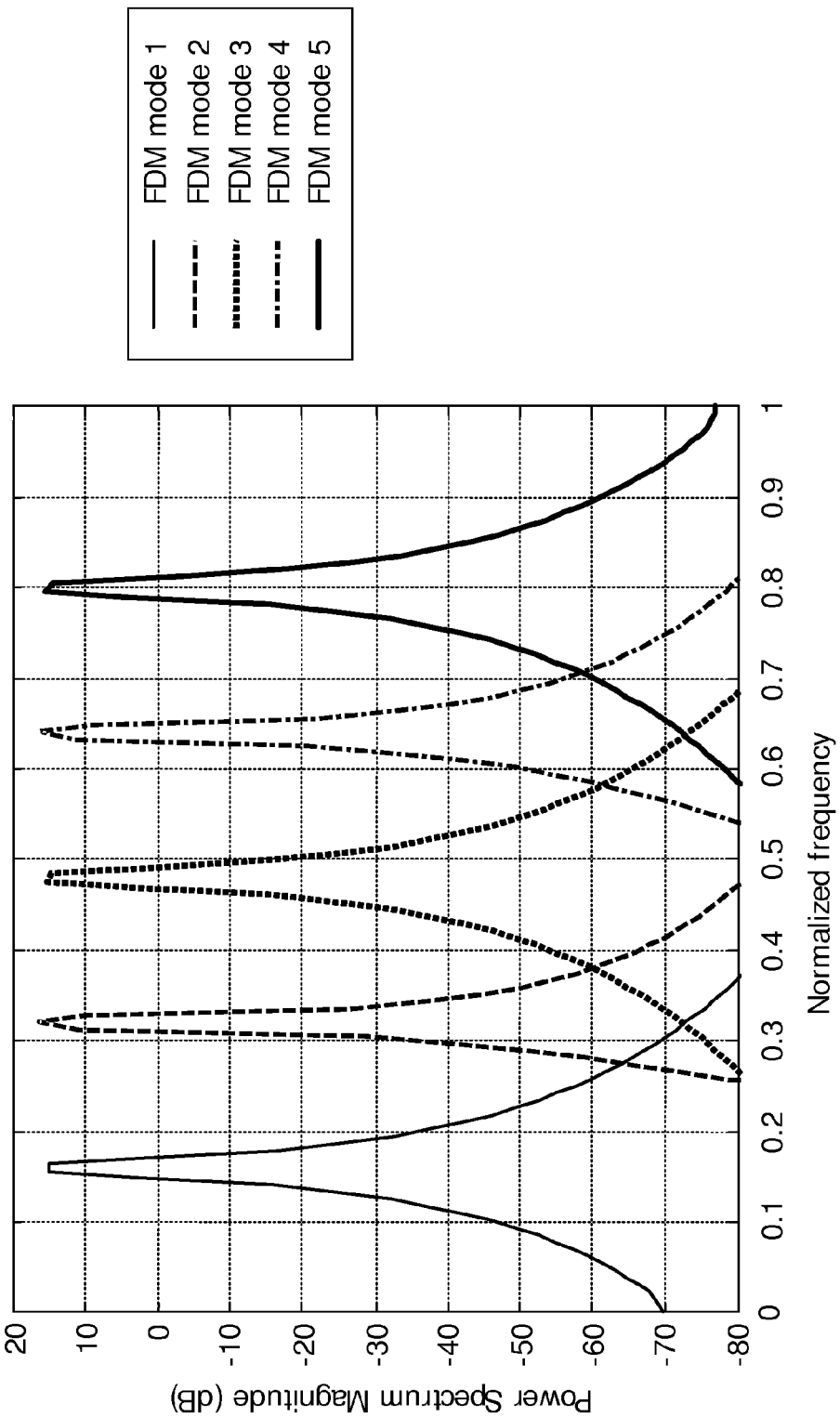
FIG. 4 shows spectra of different FDM modes according to an embodiment of the invention.

According to a first embodiment of the invention, the fact is applied that the system can operate at different frequencies or FDM modes. These FDM modes, as illustrated in FIG. 4, are approximately orthogonal in the frequency domain. When the experienced interference is spectral coloured, there exists a mode, which minimizes the experienced interference. Further, it should be noted that a TDM system can be interpreted as also operating at a single or multiple FDM modes.

The system operation frequency (fm) is adapted to a band where interference is low by evaluating the demodulator output (y). To that end, first the light source is turned off, then the demodulation frequency of the system is adapted, such that the demodulator output is minimized or becomes lower than a predefined threshold, and subsequently the modulation frequency is changed accordingly.

The method can either alternate periodically between attenuation measurements and frequency adaptation, or an adaptation phase can be initiated based on the analysis of the demodulator output signal. The frequencies to be considered can be a discrete set or continuous within a certain range. The processing unit can either adapt the demodulation frequency until some selection criterion is fulfilled, e.g. a certain minimum SIR is obtained; or evaluate the entire range or set of frequencies and then select the optimum; or evaluate the predefined frequency space by a search algorithm.

A respective behaviour can also be realized according to another embodiment of the invention by directly evaluating the spectrum of the received signal, i.e. before demodulating the signal, and selecting a frequency or frequency set where interference is low. To that end, first the light is turned off, and then the power spectrum of the received signal (x) is determined using a discrete Fourier transform. Subsequently, a modulation and corresponding demodulation frequency (fm) is selected from the minimum of the power spectrum or by applying a threshold to the power spectrum.

Again the method can either alternate periodically between attenuation measurements and frequency adaptation, or an adaptation phase can be initiated based on the analysis of the received signal or the demodulator output signal, e.g. by variations in instantaneous power.

Alternatively, the modulation frequency (fm) can be changed continuously by cycling through a certain discrete set of at least two frequency modes or frequency bands, i.e. by frequency hopping. In this case, the set of frequencies is adapted in order to avoid interference by modulated ambient light. Generally, the ambient light modulation spectrum does not cover the entire frequency set, and it can be assumed that at least one of the modulation frequencies is free of interference. To that end, the frequency set should be chosen initially such that sufficient spectral diversity is guaranteed. Therefore the detected light for at least one of the frequencies in the set, i.e. the one that is free of disturbance, results in a maximum attenuation measurement. Clearly, for a given colour of light, attenuation measurements are independent of the modulation frequencies. Now, if another frequency in the set results in a lower attenuation measurement, this is a result of interference in that modulation frequency band, and the corresponding frequency should be replaced.

In principle, a new frequency in the set can be chosen arbitrarily or based on some selection criterion. Spectral sensing, as described in the previous embodiment, may be applied to select the initial set for frequency hopping and also to replace frequencies in the set. In order to achieve this functionality, the light source does not have to be turned off, and a new modulation frequency or a set can be selected while another modulation frequency is being used. It should be noted, that it is especially preferred that only two frequencies are used, wherein the second modulation frequency is chosen from the spectrum when the attenuation is measured using the first frequency and vice versa, thereby continuously seeking the optimal modulation frequency.

The advantage of such adaptive modulation frequency hopping is that the method is based on the quasi-simultaneous evaluation of the received signal at multiple frequencies, thereby allowing continuous measurement without interruption by an adaptation phase.

According to another embodiment of the invention, CDM is used, wherein the different light sources use unique, preferably orthogonal, codes to enable the light detector to distinguish their light contributions. Suitable orthogonal codes are e.g. Walsh-Hadamard (WH) codes, where the number of light sources that can be accommodated is roughly equal to the length of the code. Next to allowing for identification of the light contributions of the different light sources, these codes also shape the spectrum of the light signal. As an example all except one WH code achieve a DC-free spectrum and their spectra are mutually different.

Figure 5:
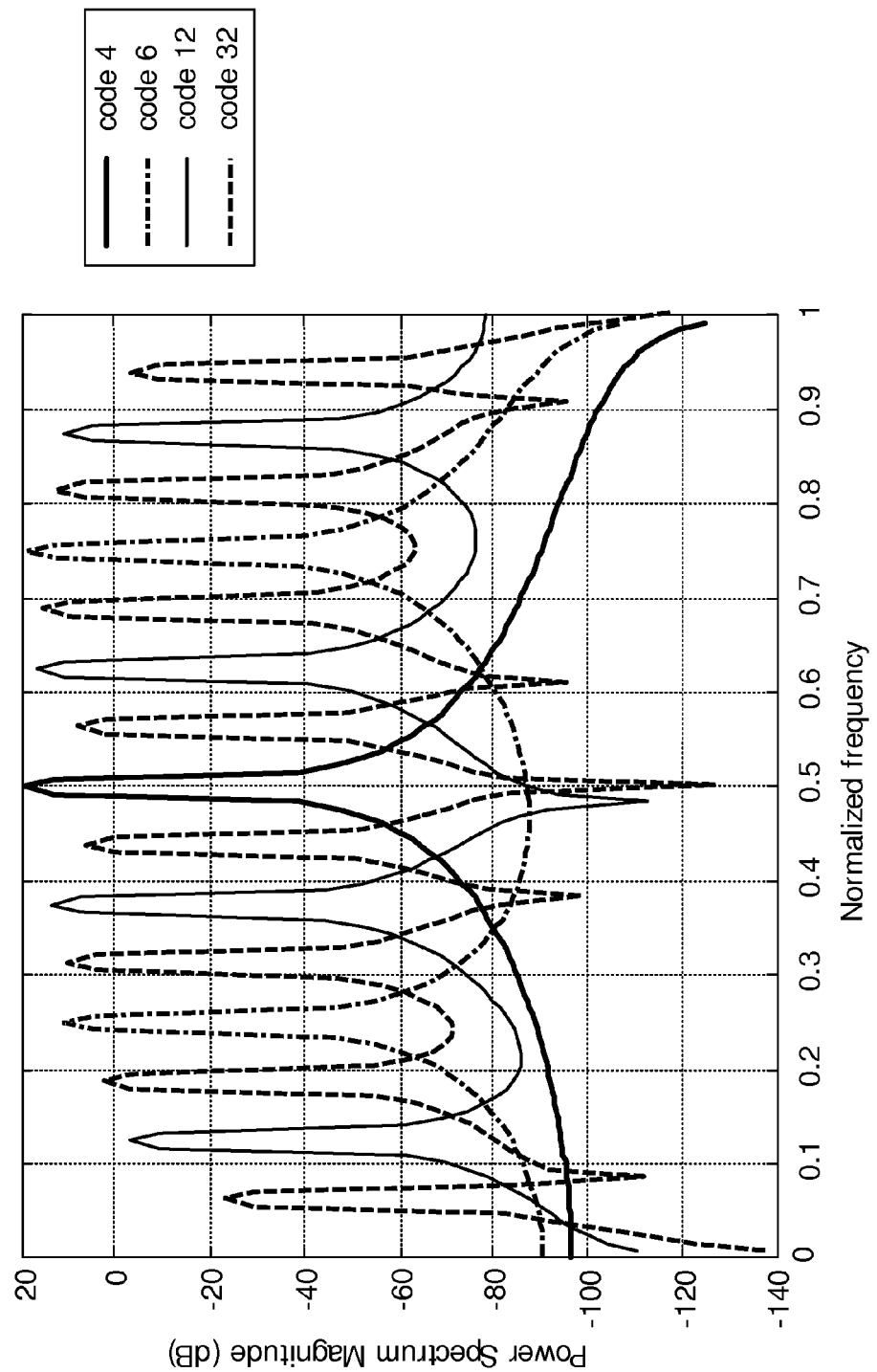
FIG. 5 shows spectra of different codes from the WH256 code book.

This is illustrated in FIG. 5 for WH codes of length 256. There, the spectra of 4 out of the 256 codes in the codebook are depicted. As can be concluded from FIG. 5, these codes have significantly different spectra. Similarly, correlation at the receiving end with the spreading codes achieves suppression of frequencies not related to the transmitted code. It should be noted that, in contrast to the frequency multiplexing illustrated in FIG. 3, the spectra achieved by these codes will generally be overlapping.

The modulation scheme is then implemented by adaptive code selection. The spreading or modulation code used by the system is adapted to the one, that is least affected by the interference, i.e. the code that is most orthogonal to the interference. This is done by evaluating the demodulator output. To that end, the technique of the first embodiment described above can be applied, where first the light is turned off, then the demodulation code of the system is adapted, such that the demodulator output is minimized or becomes lower than a certain threshold, and subsequently the transmitter spreading code is changed accordingly.

It should be noted that also the accuracy/reliability of the attenuation measurement can be scaled in such a solution by applying codes with different codes lengths, i.e. when the level of interference is low, a short code is used and when it is high, a higher code length is used. The advantage of longer codes is that they achieve better spectral shaping and thus yield a better noise and interference suppression at the receiving end. The advantage of short codes is that they reduce the measurement time.

Above embodiments have been described for a single light source. In these solutions the system searches for the optimal modulation frequency/code. For a system with N light sources, however, the system finds a set of N codes/frequencies for which the impact of the interference and noise is minimized/below a certain threshold. Here it is possible to choose to minimize the worst-case error for one of the light sources or the average error for all light sources, depending on the operation mode.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method of monitoring a vital parameter of a patient by measuring attenuation of light emitted onto tissue of the patient, comprising:
   modulating light according to a modulation mode;
   emitting the modulated light onto the tissue of the patient;
   collecting ambient light and light which is transmitted through the tissue and reflected from the tissue;
   demodulating the collected light according to the modulation mode;
   analyzing the demodulated collected light with regard to a contribution of the ambient light;
   determining a modulation mode for which the contribution of the ambient light is minimized or falls under a predefined threshold; and
   setting the modulation mode for modulating the light according to the determined modulation mode for which the contribution of the ambient light is minimized or falls under a predefined threshold.

2. The method according to claim 1, wherein the modulation mode is at least one of a modulation frequency and a modulation code.

3. The method according to claim 2, wherein the step of emitting light onto the tissue of the patient is interrupted for a predefined interruption time period; and
   during this interruption time period the collected light is successively demodulated with different modulation frequencies; and
   the modulation frequency for which the output of demodulating the collected light is minimized or falls under a predefined threshold is determined to be the modulation frequency for the light emitted onto the tissue of the patient after the predefined interruption time period.

4. The method according to claim 3, wherein the different modulation frequencies are a discrete set of frequencies or are continuous within a predefined range.

5. The method according to claim 3, wherein the step of emitting light onto the tissue of the patient is periodically interrupted.

6. The method according to claim 2, wherein the step of emitting light onto the tissue of the patient is interrupted for a predefined interruption time period; and
   during this interruption time period the collected light is successively demodulated with different modulation codes; and
   the modulation code for which the output of demodulating the collected light is minimized or falls under a predefined threshold is determined to be the modulation code for the light emitted onto the tissue of the patient after the predefined interruption time period.

7. The method according to claim 6, wherein in response to the step of analyzing the demodulated collected light with regard to the contribution of the ambient light yielding a lower level of contribution, a shorter modulation code is applied than would be in the case that the step of analyzing the demodulated collected light with regard to contribution of the ambient light yielding a higher level of contribution, in which case a longer modulation code is applied.

8. The method according to claim 2, wherein the step of emitting light onto the tissue of the patient is interrupted for a predefined interruption time period; and
   during this interruption time period the power spectrum of the collected light is determined using a Fourier transform; and
   the frequency for which the power spectrum is determined to have its minimum or a frequency for which the power spectrum falls below a predefined threshold is determined to be the modulation frequency for the light emitted onto the tissue of the patient after the predefined interruption time period.

9. The method according to claim 2, wherein the modulation frequency of the light emitted onto the tissue is consecutively changed by cycling through a predefined set of at least two frequency modes or frequency bands; and
   the modulation frequency for which the output of demodulating the collected light is maximized or exceeds a predefined threshold is determined to be the active modulation frequency for the light emitted onto the tissue of the patient.

10. The method according to claim 9, wherein during the step of emitting light onto the tissue of the patient with a first modulation frequency, a second modulation frequency is selected from a predefined spectrum.

11. The method according to claim 1, wherein the light emitted onto tissue of the patient includes at least a first light and a second light, wherein the wavelength of the first light is different from the wavelength of the second light, and wherein the first light and the second light are multiplexed.

12. The method according to claim 11, wherein at least one of time division multiplexing, frequency multiplexing, and code division multiplexing is applied.

13. The method according to claim 11, wherein the step of determining a modulation frequency and a modulation code for which the contribution of the ambient light is minimized or falls under a predefined threshold is performed for one of the first light, the second light, or an average of the first light and the second light.

14. A device for monitoring a vital parameter of a patient by measuring attenuation of light emitted onto tissue of the patient, the device comprising:
   a light modulator configured to modulate the light according to a modulation mode;
   a light emitter configured to emit the modulated light onto the tissue of the patient;
   a light detector configured to detect ambient light and light which is transmitted through the tissue and reflected from the tissue;
   a light demodulator configured to demodulate the collected light according to the modulation mode;
   an interference analyzer configured to analyze the demodulated collected light with regard to the contribution of the ambient light; and
   a processing unit configured to determine a modulation mode for which the contribution of the ambient light is minimized or falls under a predefined threshold and set the modulation mode for modulating the light according to the determined modulation mode for which the contribution of the ambient light is minimized or falls under a predefined threshold.

15. The device according to claim 14, wherein the light emitter comprises at least two light sources for emitting light with two different wavelengths.

16. The device according to claim 14, wherein the modulation mode is at least one of a modulation frequency and a modulation code.

17. An apparatus for monitoring a vital parameter of a patient, the apparatus comprising:
   one or more processor configured to:
      control a light modulator to modulate the light according to a modulation mode;
      control a light emitter to emit the modulated light onto the tissue of the patient;
      control a light detector to detect ambient light and light which is transmitted through the tissue and reflected from the tissue;
      control a light demodulator to demodulate the collected light according to the modulation mode;
      control an interference analyzer to analyze the demodulated collected light with regard to the contribution of the ambient light; and
      determine a modulation mode for which the contribution of the ambient light is minimized or falls under a predefined threshold and set the modulation mode for modulating the light according to the determined modulation mode for which the contribution of the ambient light is minimized or falls under a predefined threshold.

18. The apparatus according to claim 17, further including:
   at least two light sources for emitting light with two different wavelengths are provided.

19. The apparatus according to claim 17, wherein the modulation mode is at least one of a modulation frequency and a modulation code.

20. The apparatus according to claim 19, wherein the modulation frequency of the light emitted onto the tissue is consecutively changed by cycling through a predefined set of at least two frequency modes or frequency bands; and
   the modulation frequency for which the output of demodulating the collected light is maximized or exceeds a predefined threshold is determined to be the active modulation frequency for the light emitted onto the tissue of the patient.

* * * * *